United States Patent
Cerwin et al.

(10) Patent No.: US 7,420,195 B2
(45) Date of Patent: Sep. 2, 2008

(54) FREQUENCY-OPTIMIZED DETECTION OF GUN MUZZLE FLASHES

(75) Inventors: Stephen A. Cerwin, Mico, TX (US); Thomas C. Untermeyer, Lakehills, TX (US); David Bing Jue Chang, Tustin, CA (US); Thomas J. Warnagiris, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 302 days.

(21) Appl. No.: 11/315,540

(22) Filed: Dec. 21, 2005

(65) Prior Publication Data
US 2008/0121827 A1     May 29, 2008

Related U.S. Application Data

(60) Provisional application No. 60/638,510, filed on Dec. 22, 2004.

(51) Int. Cl.
*F23N 5/08*     (2006.01)

(52) U.S. Cl. ............... 250/554; 250/214.1; 250/339.15; 89/1.11; 356/313

(58) Field of Classification Search ............. 250/206.1, 250/206.2, 208.2, 208.6, 214.1, 221, 222.1, 250/554, 338.1, 339.15; 356/303, 313–316, 356/939; 89/1.11
See application file for complete search history.

(56) References Cited

U.S. PATENT DOCUMENTS 7,230,221 B2 * 6/2007 Busse et al. .............. 250/203.6

OTHER PUBLICATIONS

Fuller, Peter W.W., "Gun Barrel Temperature Study Using Short Time Scan Thermal Imaging", Sep. 1989, Instrumentation in Aerospace Simulation Facilities, 1989. ICIASF '89 Record., International Congress on, pp. 159-167.*

* cited by examiner

*Primary Examiner*—Georgia Y. Epps
*Assistant Examiner*—Francis M Legasse Jr.
(74) *Attorney, Agent, or Firm*—Baker Botts LLP (57) ABSTRACT

Methods for remotely detecting a gun muzzle flash, using frequency-optimized detection methods. Small explosive charges are best detected at I/R and visible wavelengths, using optical detectors, whereas large explosive charges may also be detected with antennas. Details of the time course and spectral properties of the flash can be used to distinguish gun muzzle flashes from other radiation.

6 Claims, 1 Drawing Sheet

*FIG. 1*

FREQUENCY-OPTIMIZED DETECTION OF GUN MUZZLE FLASHES

CROSS-REFERENCE TO RELATED APPLICATIONS

This application claims the benefit of U.S. Provisional Application Ser. No. 60/638,510 filed Dec. 22, 2004, which is incorporated herein by reference in its entirety.

TECHNICAL FIELD OF THE INVENTION

This invention relates to remote detection of a gun that has just launched a projectile, and more particularly to detection of the muzzle flash by detecting electromagnetic radiation from the flash.

BACKGROUND OF THE INVENTION

The remote detection of a gun that has just launched a projectile is of interest in both military and civil situations. Immediate and accurate location of a firing gun enables retaliatory action to remove the threat. It also makes feasible the deployment of protective systems. This is of great interest both in large conventional battlefield maneuvers and in the growing number of isolated sniper and ambush-type situations.

A literature survey of discussions of electromagnetic radiation from detonation of conventional explosives is contained in a report by Jonathon E. Fine and Stephen J. Vinci, "Causes of Electromagnetic Radiation from Detonation of Conventional Explosives: A Literature Survey", Army Research Lab Adelphi, (December, 1998), also available at www.stormingmedia.us/cgi-bin/04/0479/A047953-83-1t.php. This report states that observers have detected radiation at frequencies as low as 0.5 Hz and up to as high as 2 GHz. Many investigators believe that the likeliest cause is charged particles created by ionization within the explosive region.

Although some modeling and observations have been reported, analysis has been crude and observations have been few. Detailed dependences of the radiation on the size of the explosive charge or with observation wavelength have not been determined. As a result, it is not clear what the optimum wavelengths are to use for observing the gun fire, or how distant the detection apparatus might be from the gun.

DETAILED DESCRIPTION OF THE INVENTION

I. Overview

The following description is directed to a method in which remote detection of gunfire is achieved by means of the electromagnetic waves emitted by the muzzle flash. For large cannon, detection can be at low as well as at high frequencies. For small arms fire, detection is in the IR and visible wavelengths to capitalize on the increased power emitted at the higher frequencies. At IR frequencies, IR detectors that give signals proportional to detector area may be used (e.g. bolometric-type), which avoids the inverse squared frequency penalty imposed by the use of resonant antennas. For the same reason, at visible frequencies, optical-type detectors with sensitivities proportional to detector area (e.g. photodiodes) can be used. Arrays and lens- or mirror-telescopic detection systems may be used to increase sensitivity and directionality.

Detectors at short (visible and IR) wavelengths do not suffer from the inverse squared frequency dependence of resonant antennas. The latter antennas are used for very strong explosive charges.

The method described herein is based on analysis of the physics of (1) detonation inside the gun barrel, (2) expansion of the resulting shock front generated at the muzzle, (3) the associated ionization of the atmosphere by the shock front to form a collision-dominated plasma, (4) radiation emitted by the plasma electrons as they collide with the ions and with the neutral molecules in the atmosphere, and (5) subsequent self absorption and transmission of the resulting electromagnetic radiation through the plasma.

The dependences of the radiation intensity on the magnitude of the radiation emitted by the explosive charge, the time course of the emitted radiation, on its spectral properties, and on observation distance can be predicted. The feasibility of remotely detecting a muzzle flash depends on these four parameters. Based on these predicted dependences, realistic broadly applicable observation parameters can be proposed in the form of simple-to-use scaling laws.

II. Underlying Physical Considerations

It is assumed that remote detection of muzzle flashes depends on:

(1) the generation of high temperature and pressure gases inside the gun barrel, (2) the resulting shock and blast wave that emerges into the air from the gases ejected from the gun muzzle, (3) the plasma around the muzzle that results from ionization of the air by the expanding blast wave, and (4) the bremsstrahlung radiation that emerges from the plasma.

The physics of each of these processes may be analyzed to obtain rough estimates of the magnitude, time course, and spectral properties of the radiation that can be detected at a large distance from a firing gun.

A. Generation of High Temperature and Pressure Inside Gun Barrel

The time course of the temperature and pressure in a gun barrel can be estimated by developing a simple model. The rate at which energy is released from the charge is described by an exponential dependence on activation energy and temperature, and balanced with the energy in the resulting gases and to the imparting of kinetic energy to the bullet. Due to the quickness of the bullet launching and the large thermal inertia of the barrel walls, radiation and conduction losses to the wall are ignored, along with any frictional losses.

When conservation laws for particle density, momentum, and energy are employed, approximate expressions can be obtained for the temperature T, pressure P, and propellant particle density n, as a function of time t and distance x down the barrel from the original charge location.

During burning of the propellant charge:

Temperature, [1]
$$T = (E_1/k_B)[(\gamma_{bg} - 1)^{-1} + (3/2)]^{-1}$$

Particle density, [2]
$$n(t) = \left(\frac{dN}{dt}\right)[(\gamma_{bg} - 1)^{-1} + (3/2)]^{1/2}(3M)^{1/2}[2AE_1^{1/2}t^{1/2}]^{-1}$$
$$= \left(\frac{dN}{dt}\right)t/(Ax)$$

Pressure, [3]
$$P(t) = \left[3M\left(\frac{dN}{dt}\right)E_1\right]^{1/2}\left[2A[(\gamma_{bg} - 1)^{-1} + (3/2)]^{1/2}t^{1/2}\right]^{-1}$$
$$= M\left(\frac{dx}{dt}\right)^2/(3xA)$$

Bullet velocity, [4]
$$\frac{dx}{dt} = \left[6\left(\frac{dN}{dt}\right)E_1\right]\left[3M\{(\gamma_{bg} - 1)^{-1} + (3/2)\}^{1/2}t^{1/2}\right]$$

Ratio of bullet kinetic energy to gas energy, [5]
$$K/U(\text{total}) = (3/2)(\gamma_{bg} - 1)$$

After the propellant burn is completed,

Temperature, $T = T_B(x_B/x)(\gamma_{bg} - 1)$ [6]

Particle density, $n = N_B/Ax$ [7]

Pressure, $P = P_B(x_B/x)\gamma_{bg}$ [8]

Velocity, $\left(\frac{dx}{dt}\right)^2 = (3N_B E_1/M)[(\gamma_{bg} - 1)^{-1} + (3/2)]^{-1}[1 +$ [9]
$$(\gamma_{bg} - 1)^{-1}\{1 - (x_B/x)^{(\gamma_{bg}-1)}\}]$$

In these expressions, $N_B$, $T_B$, $P_B$, and $x_B$ refer to the number of propellant product molecules, temperature, pressure, and distance down barrel from original charge when all the charge has been burned. The quantity $\gamma_{bg}$ is the ratio of specific heats at constant pressure and temperature of the barrel gas; dN/dt is the rate at which propellant product particles are added to the barrel, $E_1$ is the energy introduced into the barrel by each product particle; $k_B$ is Boltzmann's constant, M is the mass of the projectile that is to be expelled from the barrel; and A is the cross sectional area of the barrel.

The distance traversed by the bullet is proportional to $t^{3/2}$ during the burn process. The ratio of the bullet's kinetic energy to the internal gas energy in the barrel at any time during the burn is $(3/2)(\gamma bg-1)$.

The equations show that after the burn, the pressure and temperature of the barrel gas decrease adiabatically, while the bullet velocity continues to increase.

The gas energy associated with the pressure and temperature given by these expressions at the end of the barrel (at the muzzle) can now be used as the initial condition for a blast wave originating from the muzzle.

Because propellant charges in modern guns are often chosen to be slow burning (to prevent damage to the barrel while efficiently using the internal energy of the propellant), it is assumed in the subsequent calculations on the blast wave that the charge is chosen so that the burn is completed just as the bullet is ejected from the barrel.

B. Blast Wave from Muzzle

The hot gas and high pressure that eject the projectile from the muzzle generate a supersonic shock wave in the air near the muzzle. The resulting expanding blast wave is in the first approximation spherical in shape, with the leading edge of the blast wave being the shock wave.

Shock Front

The shock front is quite thin, and can be approximated as a one-dimensional structure. The Rankine-Hugoniot relations for a one-dimensional shock wave in air give the temperature, pressure, density, and velocity jumps at the shock. Designating by $M_x$ the Mach number of the shock and by $v_x$ the thermal velocity in front of the shock, these relations in air are:

Temperature jump, $T_y/T_x = \{5 + M_x^2\}\{7M_x^2 - 1\}[36M_x^2]^{-1}$ [10]

Pressure jump, $T_y/P_x = [7M_x^2 - 1]/6$ [11]

Density jump, $T_y/\rho_x = 6M_x^2[5 + M_x^2] - 1$ [12]

Flow velocity following shock, [13]
$u/v_x = 5(M_x^2 - 1)/6M_x$

The subscript y denotes the quantities immediately in back of the shock. The subscript x denotes the quantities immediately in front of the shock.

At high Mach numbers, the case of interest for gunfire, the relations become even simpler:

Temperature jump, $T_y/T_x => (7/36)M_x^2$ when $M_x^2 >> 1/7$ [14]

Pressure jump, $T_y/P_x = (7/6)M_x^2$ when $M_x^2 >> 5$ [15]

Density jump, $\rho_y/\rho_x = 6$ when $M_x^2 >> 5$ [16]

Flow velocity following shock, [17]
$u/v_x = (5/6)M_x$ when $M_x^2 >> 1$

These expressions show that in a high Mach number shock wave, the air is compressed to 6× its normal density. The shock is also seen to greatly heat the air.

The above relations are useful in deriving approximate scaling laws for the behavior of a spherical blast wave in air. In particular, combining energy conservation with the Rankine-Hugoniot relations, it can be seen that a spherical blast wave has a radius that increases as $t^{2/5}$ at very high Mach numbers.

Blast Wave Profile

The density, pressure, and temperature drop off adiabatically behind the shock front. Both a triangular and a thin shell [Taylor Sedlow] approximation of the blast wave profile can be considered. The thin shell model shows that the high temperature and high pressure region has a thickness of only R/18. This corresponds to a fraction ξ of the sphere occupied by the shock-produced high temperature and pressure of:

ξ=1/6 [18]

In the limit of high Mach numbers, both the pressure and density decrease as $1/R^3$. The Mach number decreases as $1/R^{3/2}$.

Initial Conditions for Blast Wave

The gun barrel results can now be combined with blast wave physics to give blast wave parameters in terms of the energy released by the propellant charge in the gun barrel. When the charge burn is completed just as the bullet is ejected from the muzzle, the initial conditions for the blast wave expansion are:

$$M_x^2 = N_B E_1 [(\gamma_{bg} - 1)^{-1} + (3/2)]^{-1} \quad [19]$$
$$(\gamma_{bg} - 1)^{-1} [\xi P_x R^3 (4\pi/3)\{(25\gamma/12) + (7/6)(\gamma-1)^{-1}\}]^{-1} =$$
$$(2/3)K(\gamma_{bg} - 1)^{-1} [\xi P_x R^3 (4\pi/3)\{(25\gamma/12) + (7/6)(\gamma-1) - 1\}] - 1$$

$$T_y/T_x = (7/48\pi)NBE_1[(\gamma_{bg} - 1) - 1 + (3/2)] - \quad [20]$$
$$1(\gamma bg - 1)^{-1}[\xi P_x R^3]^{-1}[(25\gamma/12) + (7/6)(\gamma - 1)^{-1}]^{-1} =$$
$$(7/72\pi)K(\gamma bg - 1) - 1[\xi P x R 3] -$$
$$1[(25\gamma/12) + (7/6)(\gamma - 1) - 1] - 1$$

$$P_y/P_x = (7/8\pi)NBE_1[(\gamma_{bg} - 1)^{-1} + (3/2)] - \quad [21]$$
$$1(\gamma_{bg} - 1) - 1[\xi P_x R^3] - 1[(25\gamma/12) + (7/6)(\gamma - 1)^{-1}]^{-1} =$$
$$(7/12\pi)K(\gamma_{bg} - 1) - 1[\xi P_x R^3] - 1[(25\gamma/12) + (7/6)(\gamma - 1)^{-1}]^{-1}$$

In these equations, $\gamma_{bg}$ denotes the ratio of specific heats for the charge burn products, $\gamma$ is the ratio of specific heats for air, and as before, $T_x$ and $P_x$ denote the ambient temperature and pressure of atmospheric air. $N_B$ is the total number of product gas molecules released into the barrel from the propellant charge burn, $E_1$ denotes the energy per charge product molecule released by the burning charge, $k_B$ is Boltzmann's constant, $T_y$ is the shock temperature, $M_x$ is the shock Mach number, and R is the shock radius. K is the kinetic energy of the bullet as it leaves the muzzle, and $\xi$ is the fraction of the sphere of radius R occupied by high temperature and high pressure gas.

Assuming these values:

$\gamma = \gamma bg = 1.4$ $T_x = 300° K$ $P_x = 106$ dynes/cm2

$\xi => 1/6$ [22]

the expressions for the initial conditions for the expanding spherical blast wave simplify:

$$M_x^2 = 2.56 \times 10^{-8} N_B E_1 / (\xi R^3) = 6.86 \times 10^{-8} K / (\xi R^3) \quad [23]$$

$$T_y(° K.) = 58.3 M_x^2 \quad [24]$$

$$P_y(dynes/cm2) = 1.167 \times 10^6 M_x^2 \quad [25]$$

Here $E_1$ and K are expressed in ergs and R in centimeters. Again, the thin shell approximation is used, such that $\xi = 1/6$.

These equations show that high Mach numbers, pressures, and temperatures result from typical gun firings.

As a numerical example, consider a canonical case for a typical rifle where the propellant energy release is $3.2 \times 10^{10}$ ergs. This corresponds to a charge that propels a 100 grain bullet at 2000 ft/sec. The initial Mach number, pressure, and shock-induced temperature are 37, 1585 atmospheres, and 79,146° K, respectively.

C. Ionization in Shock Wave

A consideration of collision, ionization, and deionization times in the blast wave supports the use of the thermal equilibrium Saha equation to calculate the degree of ionization of the air due to the high shock temperature. Most of the ionization results from the oxygen molecules, since their ionization energy is much lower than that of the nitrogen molecules. Quite large degrees of ionization can result in the initial stages of the expansion.

The degree of ionization in a plasma in thermal equilibrium with its source atoms was considered by M. N. Saha [M. N. Saha, Phil.Mag.40, 472 (1920)]. Saha considered singly ionized atoms in equilibrium with neutral atoms, and demonstrated that in thermal equilibrium, the balance of ionization and deionization processes gave rise to an ionization density given by:

$$\Gamma(x) = X^2/(1-X^2) = 3.10 \times 10^{-7} (T^{2.5}/p) \exp\{-eV_i/k_B T\} \quad [26]$$

In this expression, X is the fraction of ionized atoms at a temperature T:

$$X = n_e/n \quad [27]$$

where $n_e$ = number density of electrons n = original number density of atoms $eV_i$ = ionization energy of the atom and T is expressed in degrees Kelvin and p is expressed in atmospheres.

The equilibrium density of oxygen in air is $n = 5.65 \times 10^{18}$ cm$^{-3}$. Ionization results primarily from the shock compression and heating of this oxygen. The time course of ionization in the spherical blast wave can be obtained by combining the variation of T and p with the outer radius of the blast wave calculated earlier with the Saha equation.

When the 12.5 volt ionization energy for $O_2$ is used, then:

$$\Gamma(X) = [4.72 \times 10^{-14}/\underline{R}^{4.5}] \exp[-1.62 \times 10^{10} \underline{R}^3] \quad [28]$$

And in terms of time:

$$\Gamma(X) = [8.62 \times 10^{-17}/\underline{t}^{1.8}] \exp[-1.084 \times 10^{12} \underline{t}^{1.2}] \quad [29]$$

In these expressions, $$\underline{R}^3 = R^3/N_B E_1 \quad [30]$$

$$\underline{t}^3 = t^3/N_B E_1 \quad [31]$$

As an example, consider the canonical rifle considered earlier:

$N_B = 2 \times 10^{22}$ propellant product molecules $E_1 = 1.6 \times 10^{-12}$ erg per propellant product molecule $N_B E_1 = 3.2 \times 10^{-10}$ erg total energy released by charge [32]

Then:

$$\Gamma(X) = [270/R^{4.5}] \exp[-0.50625 R^3] \quad [33]$$

where the blast wave outer radius R is expressed in cm, and $$\Gamma(X) = [1.72 \times 10^{-10}/t^{1.8}] \exp[-6.823 \times 10^7 t^{1.2}] \quad [34]$$

where time, t, is expressed in seconds. The corresponding degree of ionization is quite large initially and decreases over a period of a few microseconds.

D. Bremsstrahlung from Blast Wave

The free electrons in the plasma suffer collisions both with the ions in the high temperature portion of the blast wave and with the concentrated density of background neutral molecules. The resulting accelerations result in considerable bremsstrahlung radiation.

Spectrum of Radiation from Detailed Balance

Since the electrons radiate into a conducting plasma, the absorption of the radiation in the blast wave itself is taken into account. A general expression that applies to both an optically thin and optically thick plasma is provided by arguments of detailed balance involving a thought experiment in which the plasma is placed in a Hohlraum. The resulting emissivity formula for the emissivity $\eta$ from a slab of thickness L is:

$$\eta = \eta_{BB}[1-R/[1-\exp(-\alpha_{abs}L)][1=R'\exp(-\alpha_{abs}L)]^{-1} \quad [35]$$

where $$\eta_{BB} = (1/2\pi)^4(2\hbar\omega^3/c^2)[\exp(\hbar\omega/2\pi k_B T) - 1]^{-1} \quad [36]$$

$$=> (1/2\pi)^4(2k_B T\omega^2/c^2) \quad \text{when } \omega \ll k_B T/\hbar \quad [37]$$

$$=> (1/2\pi)^4(2\hbar\omega^3/c^2)\exp(-\hbar\omega/2\pi k_B T) \quad \text{when } \omega \ll k_B T/\hbar \quad [38]$$

is the blackbody spectral emissivity, R is the reflection coefficient for a wave impinging on the plasma, R' is the reflection coefficient for a wave leaving the plasma, and $\alpha_{abs}$ is the absorption coefficient for a wave inside the plasma. The units of $\eta$ are ergs/cm$^2$/sec/sec$^{-1}$/steradian.

For a sharp boundary, as is the case when the shock front forms the boundary:

$$R' = R \quad [39]$$

In general, the reflection coefficients and the absorption coefficient will all depend on frequency.

The flux F df in the frequency interval df at a distance D from the blast wave when its radius is R is given by:

$$F\,df = 2\pi\eta(R/D)^2\,df\,\text{ergs/cm}^2/\text{sec} \quad [40]$$

where the factor of $2\pi$ comes from the conversion from $d\omega$ to df.

The above shows that the maximum possible radiation flux is that for a blackbody. Also, in general, blackbody radiation is reduced by reflection and absorption.

Radiation from an Optically Thin Blast Wave

When $\alpha_{abs}L \ll 1$, the plasma is optically thin, and the emissivity formula [Equation (35)] simplifies. Specifically, if the thin high temperature and high pressure region of the spherical blast wave is optically thin, the emission is reduced from the black body radiation emission by $\alpha_{abs}R/18$, where R/18 is the approximate shell thickness of the high temperature and high pressure portion of the blast wave.

Radiation from an Optically Thick Blast Wave

On the other hand, if the blast wave's high temperature and high pressure region is an optically thick plasma, the emission is reduced from blackbody radiation by the factor 1-R, where R is the surface reflection coefficient at the shock front.

Frequency-dependent Absorption and Reflection Coefficient

At any one time, the blast wave plasma can be both optically thick and optically thin, and can be both transmissive and reflecting. This is because the relevant coefficients are frequency-dependent.

Dispersion Relation for Bremsstrahlung in a Plasma

The frequency dependence of the reflection and absorption coefficients can be determined from the dispersion relation for a wave propagating through the plasma. A simple (Krook collision operator) model can be used to give a simple approximate expression for the dispersion relation, taking into account collisions with both the neutral molecules and the ions. The Krook model gives the dispersion relation for an electromagnetic wave of wave number k and angular frequency $\omega$ propagating through a plasma of angular plasma frequency, p, and collision frequency, v:

$$k^2 = (1/c^2)[\omega^2 - i(\omega\omega p^2/(i\omega+\nu)] \quad [41]$$

Here c denotes the speed of light in vacuum.

Absorption Coefficient

The form of the frequency dependence of the absorption coefficient depends on whether the frequency is less than or greater than the collision frequency, and also on the relationship of these two frequencies to the plasma frequency. Four approximate expressions are obtained that cover the range of possible ratios:

Frequencies less than collision frequency:

Very low [42]

When $\omega \ll \nu$ and $\omega \ll \omega_p^2/\nu$ $\alpha\text{abs} => 2^{3/2}(1/c)(\omega\omega_p^2/\nu)^{1/2}$ Moderately low [43]

When $\omega_p^2/\nu \ll \omega \ll \nu$ $\alpha\text{abs} => 2\omega_p^2/(2c\nu)$ Frequencies greater than collision frequency:

Moderatly high [44]

When $\omega_p \gg \omega \gg \nu$ $\alpha\text{abs} => 2\omega_p/c$

Very high [45]

When $\omega \gg \nu$ and $\omega \gg \omega_p$ $\alpha\text{abs} => \omega_p^2\nu/(\omega^2 c)$ Reflection Coefficient Similarly, approximate expressions can be obtained from the dielectric constant $\in$ associated with Krook model for the reflection coefficient in different frequency ranges.

$$R = |[\in -1][\in +1]^{-1}|^2 \quad [46]$$

With the Krook model, this becomes:

$$R = [1 + 4\omega^2(\omega^2 + \nu^2 - \omega_p^2)\omega_p^{-4}]^{-1} \quad [47]$$

For the reflection coefficient behavior, it is necessary to consider six different ranges:

If $\omega^2 \ll \nu^2 \ll \omega_p^2$   $R => [1 - 4\omega 2\omega_p^{-2}]^{-1}$   $=> 1$   [48]

If $\omega^2 \ll \omega_p^2 \ll \nu^2$   $R => [1 + 4\omega^2\nu^2\omega_p^{-4}]^{-1}$   [49]

If $\nu^2 \ll \omega^2 \ll \omega_p^2$   $R = [1 - 4\omega 2\omega_p^{-2}]^{-1}$   $=> 1$   [50]

If $\omega_p^2 \ll \omega^2 \ll \nu^2$   $R => [1 + 4\omega^2\nu^2\omega_p^{-4}]^{-1}$   [51]

If $\nu^2 \ll \omega_p^2 \ll \omega^2$   $R = [1 + 4\omega 4\omega_p^{-4}]^{-1}$   $\ll 1$   [52]

If $\omega_p^2 \ll \nu^2 \ll \omega^2$   $R => [1 + 4\omega 4\omega_p^{-4}]^{-1}$   $\ll 1$   [53]

Equations [48]-[53] show that at very high frequencies, the reflection coefficient can be small. At some low and intermediate frequencies, the magnitude depends on the relative magnitudes of $\omega^2$, $\nu^2$ and $\omega_p^2$.

Equations [42]-[53] can be combined to give the approximate behavior of the absorption coefficient $\alpha^{abs}$ and the reflection coefficient R (or of more interest, the transmission coefficient 1-R) as frequency is varied from low to high values. These results are displayed below:

| | | | |
|---|---|---|---|
| $\omega \ll \nu \ll \omega_p$ | $\alpha_{abs} = (2^{3/2}/c)(\omega \omega p^2/\nu)^{1/2}$ | $1 - R = -4(\omega/\omega_p)^2 \ll 1$ | [54] |
| $\omega \ll \omega_p^2/\nu,\ \omega_p \ll \nu$ | $\alpha_{abs} = (2^{3/2}/c)(\omega \omega p^2/\nu)^{1/2}$ | $1 - R = 4\omega^2\nu^2[\omega_p^4 + 4\omega^2\nu^2]^{-1} \ll 1$ | [55] |
| $\omega_p^2/\nu \ll \omega \ll \omega_p \ll \nu$ | $\alpha_{abs} = \omega_p^2/c\nu$ | $1 - R = 4\omega^2\nu^2[\omega_p^4 + 4\omega^2\nu^2]^{-1} \to 1$ | [56] |
| $\omega_p \ll \omega \ll \nu$ | $\alpha_{abs} = \omega_p^2/c\nu$ | $1 - R = 4\omega^2\nu^2[\omega_p^4 + 4\omega^2\nu^2]^{-1} \to 1$ | [57] |
| $\nu \ll \omega \ll \omega_p$ | $\alpha_{abs} = \omega_p/c$ | $1 - R = -4\omega^2[\omega_p^2 - 4\omega^2]^{-1} \ll 1$ | [58] |
| $\nu \ll \omega_p \ll \omega$ | $\alpha_{abs} = \omega_p^2\nu/\omega^2 c$ | $1 - R = 4\omega^4[\omega_p^4 + 4\omega^4]^{-1} \to 1$ | [59] |
| $\omega_p \ll \nu \ll \omega$ | $\alpha_{abs} = \omega_p^2\nu/\omega^2 c$ | $1 - R = 4\omega^4[\omega_p^4 + 4\omega^4]^{-1} \to 1$ | [60] |

Equations [54]-[60] show that at the lowest frequencies the absorption coefficient varies as $\omega^{1/2}$, at intermediate frequencies the absorption coefficient is independent of frequency, and at the highest frequencies, the absorption coefficient varies as $\omega^{-2}$. At the lowest frequencies, the transmission coefficient is very small, while at the highest frequencies, it approaches unity.

The equations further show two conditions where the transmission coefficient is negative and small. It is not clear that this is physical, and in fact, in the blast wave, these two circumstances do not appear to arise.

Possible Emissivity Forms

When the different forms of the absorption and reflection coefficients are combined with the general expression for radiation from a plasma, 28 possible forms of the emissivity result. Of these, several have the same frequency dependence, although the constants of proportionality are different.

These 28 combinations are displayed in Table 1 to suggest the possible approximate spectral forms for bremsstrahlung from a plasma.

TABLE 1

| | $\alpha_{abs}L \ll 1$ | $\hbar\omega/2\pi k_B T \ll 1$ |
|---|---|---|
| A. | | |
| A1. | $\omega \ll \nu \ll \omega_p$ | $\eta = (1/2\pi)^4(2k_B T\omega^2/c^2)(2^{3/2}/c)(\omega\omega_p^2/\nu)^{1/2}L$ |
| A2. | $\omega \ll \omega_p^2/\nu\ \&\ \omega_p \ll \nu$ | $\eta = (1/2\pi)^4(2k_B T\omega^2/c^2)(2^{3/2}/c)(\omega\omega_p^2/\nu)^{1/2}L$ |
| A3. | $\omega_p^2/\nu \ll \omega \ll \omega_p \ll \nu$ | $\eta = (1/2\pi)^4(2k_B T\omega^2/c^2)\omega_p^2 L/c\nu$ |
| A4. | $\omega_p < \omega \ll \nu$ | $\eta = (1/2\pi)^4(2k_B T\omega^2/c^2)\omega_p^2 L/c\nu$ |
| A5. | $\nu \ll \omega \ll \omega_p$ | $\eta = (1/2\pi)^4(2k_B T\omega^2/c^2)2\omega_p L/c$ |
| A6. | $\nu \ll \omega_p \ll \omega$ | $\eta = (1/2\pi)^4 2k_B T\omega_p^2 \nu L/c^3$ |
| A7. | $\omega_p \ll \nu \ll \omega$ | $\eta = (1/2\pi)^4 2k_B T\omega_p^2 \nu L/c^3$ |
| B. | | |
| B1. | $\omega \ll \nu \ll \omega_p$ | $\eta = (1/2\pi)^4(2\hbar\omega^3/c^2)\exp(-\hbar\omega/2\pi k_B T)(2^{3/2}/c)(\omega\omega_p^2/\nu)^{1/2}L$ |
| B2. | $\omega \ll \omega_p^2/\nu\ \&\ \omega_p \ll \nu$ | $\eta = (1/2\pi)^4(2\hbar\omega^3/c^2)\exp(-\hbar\omega/2\pi k_B T)(2^{3/2}/c)(\omega\omega_p^2/\nu)^{1/2}L$ |
| B3. | $\omega_p^2/\nu \ll \omega \ll \omega_p \ll \nu$ | $\eta = (1/2\pi)^4(2\hbar\omega^3/c^2)\exp(-\hbar\omega/2\pi k_B T)\ \omega_p^2 L/c\nu$ |
| B4. | $\omega_p < \omega \ll \nu$ | $\eta = (1/2\pi)^4(2\hbar\omega^3/c^2)\exp(-\hbar\omega/2\pi k_B T)\ \omega_p^2 L/c\nu$ |
| B5. | $\nu \ll \omega \ll \omega_p$ | $\eta = (1/2\pi)^4(2\hbar\omega^3/c^2)\exp(-\hbar\omega/2\pi k_B T)2\omega_p L/c$ |
| B6. | $\nu \ll \omega_p \ll \omega$ | $\eta = (1/2\pi)^4 2\hbar\omega\exp(-\hbar\omega/2\pi k_B T)\ \omega_p^2 \nu L/c^3$ |
| B7. | $\omega_p \ll \nu \ll \omega$ | $\eta = (1/2\pi)^4 2\hbar\omega\exp(-\hbar\omega/2\pi k_B T)\ \omega_p^2 \nu L/c^3$ |
| C. | | |
| C1. | $\omega \ll \nu \ll \omega_p$ | $\eta = -(1/2\pi)^4(2k_B T\omega^2/c^2)(\omega 2/\omega p)2$ |
| C2. | $\omega \ll \omega_p^2/\nu\ \&\ \omega_p \ll \nu$ | $\eta = (1/2\pi)^4(2k_B T\omega^2/c^2)4\omega^4\nu^2\omega_p^{-4}$ |
| C3. | $\omega_p^2/\nu \ll \omega \ll \omega_p \ll \nu$ | $\eta = (1/2\pi)^4(2k_B T\omega^2/c^2)$ |
| C4. | $\omega_p < \omega \ll \nu$ | $\eta = (1/2\pi)^4(2k_B T\omega^2/c^2)$ |
| C5. | $\nu \ll \omega \ll \omega_p$ | $\eta = -(1/2\pi)^4(2k_B T\omega^2/c^2)4\omega^4\omega_p^{-2}$ |
| C6. | $\nu \ll \omega_p \ll \omega$ | $\eta = (1/2\pi)^4(2k_B T\omega^2/c^2)$ |
| C7. | $\omega_p \ll \nu \ll \omega$ | $\eta = (1/2\pi)^4(2k_B T\omega^2/c^2)$ |
| D. | | |
| D1. | $\omega \ll \nu \ll \omega_p$ | $\eta = -(1/2\pi)^4(2\hbar\omega^5/c^2)\exp(-\hbar\omega/2\pi k_B T)4/\omega_p^2$ |
| D2. | $\omega \ll \omega_p^2/\nu\ \&\ \omega_p \ll \nu$ | $\eta = (1/2\pi)^4(2\hbar/c^2)\exp(-\hbar\omega/2\pi k_B T)4/\omega 5\nu 1\omega_p^{-4}$ |
| D3. | $\omega_p^2/\nu \ll \omega \ll \omega_p \ll \nu$ | $\eta = (1/2\pi)^4(2\hbar\omega^3/c^2)\exp(-\hbar\omega/2\pi k_B T)$ |
| D4. | $\omega_p < \omega \ll \nu$ | $\eta = (1/2\pi)^4(2\hbar\omega^3/c^2)\exp(-\hbar\omega/2\pi k_B T)$ |
| D5. | $\nu \ll \omega \ll \omega_p$ | $\eta = -(1/2\pi)^4(2\hbar\omega^3/c^2)\exp(-\hbar\omega/2\pi k_B T)4\omega^5\omega_p^{-2}$ |

TABLE 1-continued

| | $\alpha_{abs}L \ll 1$ | $h\omega/2\pi k_B T \ll 1$ |
|---|---|---|
| D6. | $\nu \ll \omega_p \ll \omega$ | $\eta = (1/2\pi)^4(2h\omega^3/c^2)\exp(-h\omega/2\pi k_B T)$ |
| D7. | $\omega_p \ll \nu \ll \omega$ | $\eta = (1/2\pi)^4(2h\omega^3/c^2)\exp(-h\omega/2\pi k_B T)$ |

The spectral form to be observed in any given situation depends on the relative values of the frequencies $\omega_p$, $\nu$, and $\omega$, as well as the values of $\alpha_{abs}L$ and $h\omega/k_B T$.

In all, the results show that there are 8 possible different spectral forms:

$\omega^0$
$\omega^2$
$\omega^{5/2}$
$\omega^4$
$\omega\exp(-h\omega/2\pi k_B T)$
$\omega^{7/2}\exp(-h\omega/2\pi k_B T)$
$\omega^3\exp(-h\omega/2\pi k_B T)$
$\omega^5\exp(-h\omega/2\pi k_B T)$ Only for cases A6 and A7 does the bremsstrahlung have the flat $\omega^0$ spectrum often cited in the literature.

total energy of $3.2 \times 10^{10}$ erg. The entries in Table 2 are for the following canonical case:

Total energy release from propellant charge:
$N^B E_1 = 3.2 \times 10^{10}$ erg

Burn completion at time 100 grain bullet leaves barrel at 2000 ft/sec [61]

For any other value of $N_B E_1$ (for a situation in which the propellant charge is chosen so that the burn is completed at the time of bullet ejection), the behavior described in the example has the same form, except that the time (and the blast wave radius) at which a particular value of temperature T, pressure P, free electron density $n_e$, angular plasma frequency $\omega_p$, collision frequency $\nu$, etc., occurs is changed according to a scaling law:

$$t' = (N_B E_1/3.2 \times 10^{10})^{1/3} t \quad [62]$$

$$R' = (N_B E_1/3.2 \times 10^{10})^{1/3} R \quad [63]$$

TABLE 2

| | |
|---|---|
| Radius of blast wae leading surface (cm) | $R = 513 t^{0.4}$ |
| Shock-induced temperature of blast wave (° K) | $T = 286,000/R^3$ |
| Pressure in blast wave (atm) | $P = 5738/R^3$ |
| Gamma $\Gamma(X) = X^2[1 - X^2]^{-1}$ | $\Gamma(X) = (270/R^{4\,5}) \exp(-0.506\,R^3)$ |
| Fractional degree of ionization | $x = \Gamma^{1/2}[1 + \Gamma]^{-1/2}$ |
| Free electron density in blast wave (cm$^{-3}$) | $n_e = 5.65 \times 10^{18}\,X$ |
| Plasma frequency (Hz) | $f_p = \omega_p/2\pi = 8970\,n_e^{1/2}$ |
| Debye shielding length (cm) | $\lambda_D = 6.90(T/n_e)^{1/2}$ |
| Electron thermal velocity (cm/sec) | $v_{thermal} = 6.74 \times 105\,T^{1/2}$ |
| Electron/neutral collision frequency (sec$^{-1}$) | $\nu_{en} = 2.076 \times 10^{11}\,T^{1/2}$ |
| Electron/ion collision frequency (sec$^{-1}$) | $\nu_{ei} = 933\,fp4\,(n_e v_{thermal}^3)^{-1}$ |
| Total collision frequency (sec$^{-1}$) | $\nu = \nu_{en} + \nu_{ei}$ |
| Wave number in plasma for $\omega$(cm$^{-1}$) | $k = (\omega/c)[1 - \omega_p^2\{\omega(\omega - i\nu)\}^{-1}]$ |
| Absorption coefficient (cm − 1) | $\alpha_{abs} = -2\,\text{Im}(k)$ |
| Blast wave high P&T layer thickness (cm) | $L = R/18$ |
| Reflection coefficient at blast wave surface | $R = [1 + 4\omega^2(\omega^2 + \nu^2 - \omega_p^2)\,\omega_p^4]^{-1}$ |
| Emissivity (erg/cm$^2$/sec/sec$^{-1}$) | $\eta = \eta_{BB}[1 - R][1 - \exp(-\alpha_{abs}L)][1 - R\exp(-\alpha_{abs}L)]^{-1}$ |
| Blackbody emissivity (erg/cm$^2$/sec/sec$^{-1}$) | $\eta_{BB} = (\frac{1}{2}\pi)4(2h\omega^3/c^2)[\exp(h\omega/2\pi k_B T) - 1]^{-1}$ |
| $=>(\frac{1}{2}\pi)^4(2\,k_B T\,\omega^2/c^2)$ | when $\omega \ll k_B T/h$ |
| $=>(\frac{1}{2}\pi)^4(2h\omega^3/c^2)\exp(-h\omega/2\pi k_B T)$ | when $\omega \gg k_B T/h$ |
| Flux in frequency interval df at a distance D (ergs/cm$^2$/sec) | $F df = 2\pi\eta(R/D)^2 df$ |

Application of the Forms to the Radiation from the Muzzle Blast Wave

As an example, for a low frequency of 10 KHz, the approximation of case A2 applies in the early stages of the blast wave expansion, whereas that of case A3 applies at later stages.

For a frequency of 1 GHz, the approximation of C2 applies initially, followed by that of A2 in the intermediate stages of the expansion, and by that of A3 in the later stages.

For 1015 Hz, the approximation of C7 is good throughout the expansion.

Spectrum and Time Course of Bremsstrahlung from a Muzzle Blast Wave

When the results on barrel and blast wave physics are combined with the radiation formulas, the properties of the bremsstrahlung from a muzzle flash can be estimated.

Table 2 is a summary of formulae for calculating radiation in canonical case of slow burning propellant that releases a III. Numerical Results for the Canonical Case Table 2 reveals several interesting features about the blast wave properties for the canonical case of Equation [61]:

Time and distance scales: The blast wave radius expands to 8 cm in 30 microseconds.

Temperature: During this period, the shock-induced temperature drops from several tens of thousands of degrees Kelvin to 567° K.

Pressure: The pressure starts at well over 1000 atmospheres, and decreases in 30 microseconds to 11 atmospheres.

Free electron density: The degree of ionization is very high during the first few microseconds, and decreases to practically zero in 10 microseconds. Thus, we would expect radiation from the free electrons to be concluded in less than 10 microseconds.

Plasma frequency: The decrease in ionization in 10 microseconds results in the plasma frequency decreasing from 1013 Hz to 537 KHz during that period.

Collision frequency with neutrals: The blast wave plasma is collision-dominated. The collision frequency of the free electrons with neutrals starts out at about well $5 \times 10^{13}$ sec$^{-1}$ and over 30 microseconds does not decrease to less than $5 \times 10^{12}$ sec$^{-1}$ (only a factor of 10).

Collision frequency with ions: The electron's collision frequency with the ionized gas is always less than that with the neutrals, starting out at about $5 \times 10^{12}$ sec$^{-1}$, but decreasing in 10 microseconds to practically nothing (corresponding to the disappearance of ionization by that time).

Ratio of collision frequency to plasma frequency: Throughout the entire 10 microseconds where there is some ionization, the collision frequency is larger than the plasma frequency. Already at 2 microseconds, it is 10 times larger, and the ratio becomes increasing larger for larger times.

Blackbody emissivity: For purposes of example herein, blackbody emissivity is considered for three representative frequencies: 10 KHz, 1 GHz, and $10^{15}$ Hz. The blackbody emissivity provides an upper bound to the actual emissivity of the blast wave plasma. Initially at 10 KHz, the emissivity is very low, but is 10 orders of magnitude larger at 1 GHz, and another nine orders of magnitude greater at the optical frequency of $10^{15}$ Hz. The variation with time is most pronounced at $10^{15}$ Hz, because there the decreasing temperature occurs in the large exponential of the blackbody function. Indeed, by the time the blast wave has expanded for 6 microseconds (out to a radius of 4 cm), the emissivity at 1015 Hz and that at 1 GHz are comparable in magnitude.

The optical thickness or thickness of the blast wave plasma may be considered at the same three representative frequencies: 10 KHz, 1 GHz, and $10^{15}$ Hz. The Table 2 entries combined with the above discussion on optical thickness show that for 10 KHz, the blast wave plasma is always optically thin ($\alpha_{abs}L \ll 1$) for all 30 microseconds displayed. For 1 GHz, the plasma is optically thick for the first 2½ microseconds of the expansion, becoming thin only after that initial period. For $10^{15}$ Hz, the plasma is optically thin throughout the expansion.

Throughout 30 microseconds of expansion (during which the free electron density decreases from greater than $10^{18}$ cm$^{-3}$ to much less than 1 cm$^{-3}$), the blackbody peak frequency remains above $10^{13}$ Hz, starting out at about $10^{15}$ Hz. Thus, microwave frequencies are always much lower than the blackbody peak frequency throughout the plasma radiation portion of the expansion, and optical frequencies are above the peak through most of the radiation process.

For the canonical case of a $3.2 \times 10^{10}$ erg propellant charge release, the primary findings are summarized below.

Ionization duration: The free electrons that radiate exist only during the first 10 microseconds of the blast wave, during which time the radius increases to 5 cm.

Collision dominated plasma: During the expansion, the collision frequency is largest with neutrals. The collision frequency is always higher than the plasma frequency, i.e. the plasma is collision-dominated.

Optical thickness: At intermediate frequencies, (e.g. 1 GHz) the plasma is optically thick in the initial stages, but becomes optically thin after about 3 microseconds. At very low frequencies (e.g. 10 KHz), and at optical frequencies, the plasma is optically thin throughout the whole expansion.

Peak blackbody frequency: The peak blackbody frequency varies from $10^{15}$ Hz initially to $10^{13}$ Hz during the expansion.

Approximate Expressions for Spectra During Expansion

The numerical results set out above suggest that of the 28 possible general spectral forms for the emissivity listed in Table 1, only 6 apply to typical muzzle blast waves. Table 3 sets out approximate emissivity formulas during muzzle blast wave expansion.

TABLE 3

Very low frequencies

Early in expansion (when $\omega \ll \omega_p^2/\nu$ & $\omega_p \ll \nu$, $\hbar\omega/2\pi k_B T \ll 1$ and $\alpha_{abs}L \ll 1$) $\eta = (1/2\pi)^4 (2k_B T\omega^2/c^2)(2^{3/2}/c)(\omega\omega_p^2/\nu)^{1/2}L$
Late in expansion ($\omega_p^2/\nu \ll \omega \ll \nu$, $\hbar\omega/2\pi k_B T \ll 1$ and $\alpha_{abs}L \ll 1$)
$\eta = (1/2\pi)^4 (2k_B T\omega^2/c^2) \omega_p^2 L/c\nu$ Intermediate frequencies Very early in expansion ($\omega \ll \omega_p^2/\nu$ & $\omega_p \ll \nu$, $\hbar\omega/2\pi k_B T \ll 1$ and $\alpha_{abs}L \gg 1$) $\eta = (1/2\pi)^4 (2k_B T/c^2)^4 \omega^4 \nu^2 \omega_p^{-4}$
Early in expansion ($\omega \ll \omega_p^2/\nu$ & $\omega_p \ll \nu$, $\hbar\omega/2\pi k_B T \ll 1$ and $\alpha_{abs}L \ll 1$) $\eta = (1/2\pi)^4 (2k_B T\omega^2/c^2)(2^{3/2}/c)(\omega\omega_p^2/\nu)1/2L$
Late in expansion ($\omega_p^2/\nu \ll \omega \ll \omega_p \ll \nu$, $\hbar\omega/2\pi k_B T \ll 1$ and $\alpha_{abs}L \ll 1$) $\eta = (1/2\pi)^4 (2k_B T\omega^2/c^2) \omega p2L/c\nu$ Very high frequencies Throughout expansion ($\omega p \ll \nu \ll \omega$, $\hbar\omega/2\pi k_B T \gg 1$ and $\alpha_{abs}L \ll 1$)
$\eta = (1/2\pi)^4 2\hbar\omega \exp(-\hbar\omega/2\pi k_B T)\omega_p^2 \nu L/c3$ In Table 3, the parameters in the approximate formulas vary during the expansion according to the expressions in Table 1. The value L should be taken to be R/18.

Numerical Example of Fluxes

With the cited numerical parameters, radiation fluxes can be calculated. At a distance of 10 meters from the gun, and at the 3 representative frequencies of 10 KHz, 1 GHz, and $10^{15}$ Hz, the respective maximum fluxes are $3 \times 10^{-32}$, $3 \times 10^{-21}$ and $10^{-9}$ erg/cm$^2$/sec/Hz, respectively. Clearly, higher frequencies benefit by being closer to the peaks of the blackbody radiation curves during the expansion.

Time Delay in Maximum Flux at Intermediate Frequencies

At the very low (10 KHz) and very high frequencies ($10^{15}$ Hz), the maximum flux occurs at the beginning of the blast wave expansion, where the temperature is the highest. However, at the intermediate frequency (1 GHz), the maximum flux does not occur until 3 microseconds into the expansion. This is when the plasma is changing from being optically thick to optically thin.

IV. Approximate Scaling Laws for Radiation Flux

The numerical results given above have been for the canonical case of Equation [61]. It is of interest to inquire how the results vary if the initial explosive charge is larger or smaller than that for the canonical case.

From the equations discussed earlier, it is straightforward to obtain approximate scaling laws if four different frequency regimes are considered: very high frequencies, high intermediate frequencies, moderate intermediate frequencies, and low intermediate frequencies. Extremely low frequencies are not of much interest, since the power radiated there is so small.

Table 4 sets out approximate expressions for bremsstrahlung radiation flux from muzzle blast wave at an observation distance of $D_{cm}$. It gives the approximate scaling laws for an arbitrary value of:

$E$=Energy released by propellant charge/$3.2 \times 10^{10}$ erg   [64]

where the $3.2 \times 10^{10}$ erg is the amount of energy released in the canonical case where a 100 grain bullet leaves the barrel at 2000 ft/sec. Table 4 also defines the four frequency regimes alluded to earlier.

The entries in Table 4 assume that the propellant charge burn is completed just as the bullet leaves the muzzle. If the burn is completed before the bullet leaves the barrel, the results are modified simply by multiplying E by the factor $(x_B/L_{barrel})^{\lambda_{gb}}$:

$$E \rightarrow E(x_B/L_{barrel})^{\lambda_{gb}} \quad [65]$$

where $x_B$ denotes the distance the bullet has traveled down the barrel, $L_{barrel}$ denotes the length of the gun barrel, and $\lambda_{gb}$ denotes the ratio of the specific heats at constant pressure and volume for the propellant gases.

TABLE 4

Very high frequencies [f > $10^{14}$ Hz]

Fdf = $3.46 \times 10^{-18}$ (f$E^{0.6}/D_{cm}^2 t^{0.3}$) exp{$-1.34 \times 10^8 (1.52 \times 10^{-16} f + 0.262)(t^{1.2}/E^{0.4})$}df$_{Hz}$  erg/cm²/sec
    High intermediate frequencies [$2.5 \times 10^{10}/E^{1/3}$ < f < $5 \times 10^{13}$ Hz]

Fdf = $1.25 \times 10^{-32}$ f²$E^{2/3}$ df$_{Hz}$/Dcm²  erg/cm2/sec
    Moderate intermediate frequencies [⅓] × 109 < f < $2 \times 10^{10}$ Hz]

Fdf = $1.35 \times 10^{-32}$ f²$E^{2/3}$ df$_{Hz}$/Dcm²  erg/cm²/sec
    Low intermediate frequencies [$3 \times 10^4/E^{2/3}$ << f << $1.8 \times 10^5/E^{1/4}$Hz]

Fdf = $1.2 \times 10^{-36}$ f$^{2.8}$ $E^{0.5}$df$_{Hz}$/Dcm²  erg/cm²/sec

For intermediate frequencies, the flux listed is the maximum flux that occurs during the expansion at the time that the blast wave plasma changes from being optically thick to being optically thin. For the very high frequency entry, the expression should apply throughout the expansion, except in the very early moments when the ionization density is very large.

In Table 4, E is the energy released by the propellant charge divided by $3.2 \times 10^{10}$ erg.

The entries assume that the propellant charge burn is completed just as the bullet leaves the muzzle. Equation [65] provides a simple modification when the propellant is used up before the bullet leaves the barrel.

V. Detector Considerations

Table 4 contains the principal results on expected radiation fluxes from a muzzle flash. To see whether remote detection of the muzzle flash is feasible, predicted fluxes are compared to the fluxes that a detector can pick up. Two types of representative detectors are: (1) resonant dipole antennas, and (2) detectors with sensitivities roughly proportional to detector area. The latter can include both thermal and photon detectors.

A. Resonant Antenna

A resonant dipole antenna has an approximate receiving cross section given by an ellipse of major diameter equal to ¾ wavelength and a minor diameter equal to ¼ diameter, and typically has about a 5% bandwidth.

Accordingly, the flux F of Table 4 can be converted into power input P to the receiver through the simple relation:

$$P = F \times (\text{antenna cross section}) \times (0.05 f) \quad [66]$$

The antenna cross section is roughly $$A = (3\pi/64)\lambda^2 = (3\pi/64)c^2/f^2 \quad [67]$$

and so $$P = 6.7 \times 10^{18} F/f \, \text{erg/sec} \quad [68]$$

Since 1 watt = $10^7$ erg/sec, the above becomes:

$$P = 6.7 \times 10^{11} F_{erg/sqcm/sec/Hz}/f_{Hz} \text{watts} \quad [69]$$

Table 5 sets out approximate expressions for muzzle flash bremsstrahlung radiation power input to a resonant dipole antenna [P=$6.7 \times 1011$ F/f watts].

TABLE 5

Very high frequencies [f > $10^{14}$ Hz]

P = $2.3 \times 10^{-6}$ ($E^{0.6}/D_{cm}^2$ t0.3) exp{$-1.34 \times 10^8 (1.52 \times 10^{-16} f + 0.262)(t^{1.2}/E^{0.4})$} watts
    High intermediate frequencies [$2.5 \times 10^{10}/E^{1/3}$ < f < $5 \times 10^{13}$ Hz]

P = $8.4 \times 10^{-21}$ f$E^{2/3}/D_{cm}^2$ watts
    Moderate intermediate frequencies [⅓] × 109 < f < $2 \times 1010$ Hz]

P = $9 \times 10^{-21}$ f $E^{2/3}/D_{cm}^2$ watts
    Low intermediate frequencies [$3 \times 10^4/E^{2/3}$ << f << $1.8 \times 105/E^{1/4}$ Hz]

P = $8 \times 10^{-25}$ f$^{1.8}$ $E^{0.5}/D_{cm}^2$watts

For the intermediate frequencies, the power listed is the maximum power that occurs during the expansion at the time that the blast wave plasma changes from being optically thick to being optically thin. For the very high frequency entry, the expression should apply throughout the expansion, except in the very early moments when the ionization density is very large.

In Table 5, E is the energy released by the propellant charge divided by $3.2 \times 10^{10}$ erg.

The entries assume that the propellant charge burn is completed just as the bullet leaves the muzzle. Equation [65] provides a simple modification when the propellant is used up before the bullet leaves the barrel.

The entries show that the power input to a resonant dipole antenna does not drop off with decreasing frequency as fast as the radiation flux does.

Numerical Example for a Resonant Dipole Antenna (for the Canonical Case of Equation 61)

As an example, at a distance of 10 meters (D=1000 cm), using Table 5:

$$P = 2 \times 10^{-24} \text{ watt at 10 KHz}$$
$$2.3 \times 10^{-18} \text{ watt at 1 GHz}$$
$$8.7 \times 10^{-13} \text{ watt at } 10^{15} \text{ Hz}$$

assuming a resonant dipole antenna could actually be fabricated at this short wavelength.

A typical receiver noise floor is −90 dBm ($10^{-12}$ watts). Thus, unless the explosives have a strength much larger than the canonical case, detection with a resonant antenna may not be feasible.

B. Detectors with Sensitivities Proportional to Area

A resonant dipole cannot take advantage of the strong increase in radiation flux with increasing frequency because of the $1/f^2$ dependence of its effective cross section. This dependence is not present in detectors whose capture of radiation energy is proportional to the detector area.

At longer wavelengths, detectors with this area proportional property include large dish antennas. At shorter wavelengths, such detectors include thermal (e.g. bolometric detection where electrical conductivity changes in response to incident radiation) and photon detectors (e.g., photovoltaic, photoconductive, photoelectromagnetic, photoconductive sensors).

As an example, consider a typical solid state detector, which can be quite sensitive. The sensitivity is often described in terms of the parameter D*, defined as the reciprocal of the noise equivalent power (NEP) of the detector referred to unit area and a 1 Hz electrical bandwidth:

$$D^* = (A_D \Delta f_E)^{1/2}/NEP \text{ watt}^{-1} \text{ cm sec}^{1/2} \quad [70]$$

where $\Delta f_E$ denotes the electrical bandwidth of the detector circuitry and AD is the detector area. The noise equivalent power is:

$$NEP = (A_D \Delta f_E)^{1/2}/D^* \quad [71]$$

Typical commercial detectors have D*'s in the range $10^8$-$10^{12}$ watt$^{-1}$ cm sec$^{1/2}$, although theoretical D*'s can be much higher, such as $10^{16}$ watt$^{-1}$ cm sec$^{1/2}$.

Compare this with the muzzle radiation fluxes discussed earlier. Consider, for example, the radiation flux for the canonical case of Equation [61] at $10^{15}$ Hz at 1 microsecond after the bullet is expelled from the barrel. The equations show this to be $F = 4.2 \times 10^{-8}/D_m^2$ erg/sec/cm² Hz, that is, $$F = 4.2 \times 10^{-15}/D_m^2 \text{ watts/cm}^2/\text{Hz} \quad [72]$$

at a distance of Dm meters from the muzzle.

Thus, for a collection area A and effective filter width $\Delta f$, the ratio of the power collected by a detector located $D_m$ meters from the nozzle would be $FA\Delta f$, and the ratio r of this signal power to the detector's noise equivalent power of Equation [71] is:

$$r = FA\Delta f D^*/(A_D \Delta f_E)^{1/2} \quad [73]$$

Suppose that:

| | | |
|---|---|---|
| Detector merit | $D^* = 10^9$ watt$^{-1}$cm sec$^{1/2}$ | [74] |
| Collection area | $A = 1$ cm² | |
| Detector area | $A_D = 1$ cm² | |
| Filter frequency width | $\Delta f = f/10 = 10^{14}$ Hz | |
| Electrical bandwidth | $\Delta f E = 10^6$ Hz | | where the electrical bandwidth is chosen to be 1 MHz because the earlier calculations indicated that the time scale of the plasma duration is of the order of several microseconds.

With these parameters and the flux given by Equation [72], the signal power is equal to the noise equivalent power at a distance $$D_m(r=1) = 650 \text{ meters} \quad [75]$$

If D* were instead equal to $10^{11}$ watt$^{-1}$ cm sec$^{1/2}$ (the upper end of values for typical commercially available detectors), then:

$$D_m(r=1) = 20,000 \text{ meters} \quad [76]$$

There appears to be no problem with remote detection at quite respectable distances with these types of short wavelength detectors.

C. Further Signal Enhancement

Signal strength can be improved even further with conventional optics. These could include telescopic lenses or mirrors. In addition, multiple detectors can be employed in arrays. There is, however, a tradeoff here between increased signal strength and reception solid angle.

For example, if an N×N phased antenna array of resonant frequency dipoles is used, then the power input can be increased by $N^2$.

VI. Active Versus Passive Detection

In accordance with the above, emissions from the muzzle flash may be detected in a passive manner. It is also possible to achieve "active" detection by flooding an area with radio waves. If the flood interacts with the plasma, the result is a recognizable reflection. Discrimination from other reflections can be made based on rise and fall time.

VII. Conclusions

1. Muzzle flashes can be detected at large distances by electromagnetic radiation emitted at IR and visible wavelengths. For small guns, remote detection at large distances should be based on detection of these higher (IR and visible) frequencies. More bremsstrahlung radiation power is available at visible frequencies, or at IR frequencies where the atmosphere has a window, rather than at longer wavelengths.

Backup: The variation with wavelength of the radiation flux produced is provided in Table 4, showing a strong increase in magnitude with increasing frequency.

2. The radiation power is dependent on the source energy. Thus, for very large explosive charges, the magnitude of long wavelength (mm wave) radiation is large enough to be detected at distances of interest.

Backup: Table 4 also shows how the radiation flux scales with the magnitude of the explosive charge. Roughly, the flux is proportional to the ⅔ power of the explosive charge.

3. When longer wavelengths can be used (large munitions), detection with resonant dipole antennas is appropriate.

Backup: Table 5 shows that a resonant dipole antenna decreases the amount by which the radiation signal drops off as the wavelength becomes longer. This arises mainly from the proportionality of the antenna cross section to the square of the wavelength 4. For shorter wavelength detection, the use of detectors that give signals roughly proportional to the detector area is proposed to avoid the inverse squared frequency penalty imposed by resonant antennas.

Backup: The discussion of Section 7b shows that the D*'s of commercially available solid state detectors is sufficient to give good signal to noise at very large distances from the muzzle.

5. The detection signals can be enhanced by use of detector arrays and optical lenses and mirrors, although their use in any given situation must be based on a trade-off between restrictions in reception solid angle and signal magnitude.

Backup: Equation [73] shows that the signal to noise is proportional to $A/A_D^{1/2}$ for a given D*, where A is the collection area provided by the optics and $A_D$ is the detector area. Thus, increasing A with respect to $A_D$ by optics provides good leverage.

6. Both the details of the time course and the spectral properties of the muzzle flash can be used to distinguish gun firing from ambient radiation and transient reflections, such as solar radiation from the windshield of a passing car.

Backup for time course: In a typical case, the free electrons that radiate exist only during the first 10 microseconds of the blast wave, during which time the radius increases to 5 cm. At very low and very high frequencies, the maximum flux occurs at the beginning of the blast wave expansion, where the temperature is the highest. However, at intermediate frequencies, the maximum flux does not occur until a few microseconds into the expansion. This is when the plasma is changing over from an optically thick to an optically thin one.

Backup for spectral information: For a typical case, the peak blackbody frequency varies from $10^{15}$ Hz initially to $10^{13}$ Hz during the expansion. Table 4 provides approximate expressions for the radiation spectrum produced by gunfire.

VIII. Method of Detecting Gun Muzzle Flashes

Figure 1:
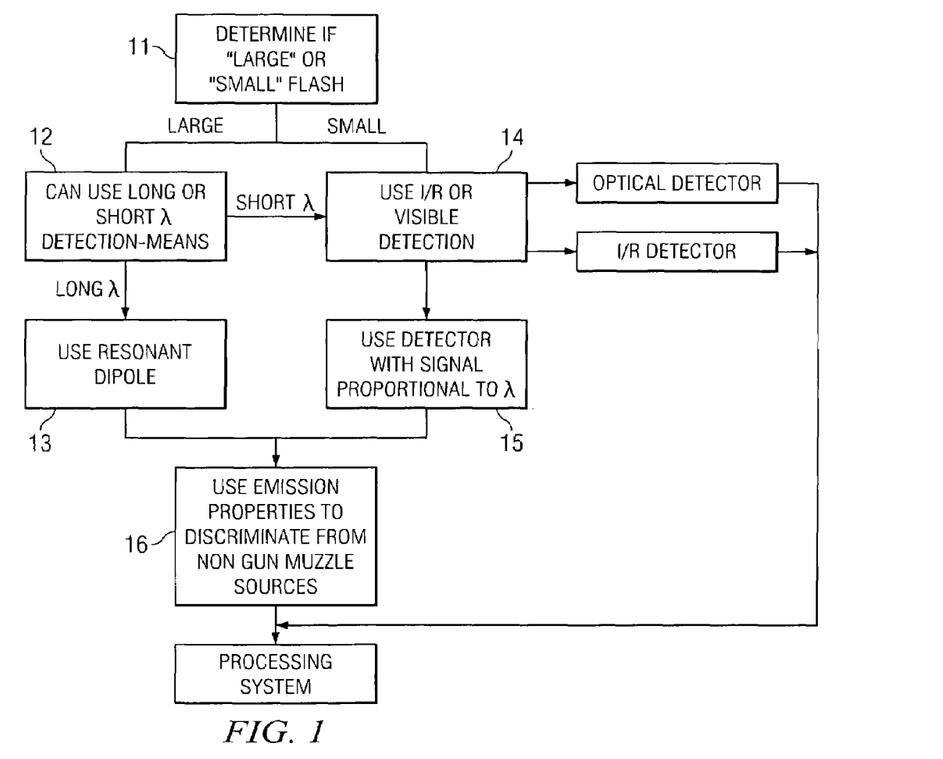
FIG. 1 illustrates a method of detecting gun muzzle flash in accordance with the invention.

FIG. 1 illustrates a method of detecting gun muzzles flashes in accordance with the invention.

In Step 11, it is determined whether the detection of interest is for a "large" or a "small" gun muzzle flash. The method of detection depends on this distinction, however, it should be understood that a detection system could incorporate means for detecting both types of gun muzzle flashes. Step 12 applies to large flashes, and permits the use of detection means suitable for either short or long wavelengths. For long wavelengths, Step 13 is detecting the flash with a dipole antenna.

Step 14 applies to small flashes, and permits the use of IR or visible detection means. In Step 15, for small flashes or large flashes with short wavelength responses, a detector having a signal proportional to wavelength is used.

In Step 16, emission properties, such as those discussed above, are used to determine whether the received signal is from a gun or a non-gun source.

The principles described above can be used to determine, for a given received signal, whether a gun has fired. The energy of the gun blast, and hence the size of the gun, and the distance of gun from the detection system, can also be estimated.

The invention claimed is:

1. A method of remotely detecting the firing of a gun, comprising:
   using a detector to receive signals representing electromagnetic radiation from the gun;
   using spectral properties of the signal to determine the blast expansion characteristics;
   using the blast expansion characteristics to estimate the propellant energy associated with the blast from the gun; and
   using properties of the signal to distinguish the signal from signals generated by non gun sources.

2. The method of claim 1, further comprising generating radio frequency waves, such that plasma from the gun interacts with the radio frequency waves.

3. The method of claim 1, wherein the detector is an optical detector for wavelengths in the visible frequency range.

4. The method of claim 1, wherein the detector is an infrared detector.

5. The method of claim 1, wherein the detector is a dipole antenna detector.

6. A detection system for remotely detecting the firing of a gun, comprising:
   an optical detector operable to receive signals from the gun in the visible frequency range;
   an infrared detector operable to receive signals from the gun in the infrared frequency range;
   a processing system operable to use properties of the signal to estimate the propellant energy associated with the blast from the gun, and to use properties of the signal to distinguish the signal from signals generated by non gun sources.

* * * * *